United States Patent [19]

Belmont

[11] Patent Number: 5,329,056
[45] Date of Patent: Jul. 12, 1994

[54] PREPARATION OF SUBSTITUTED CYCLOPENTADIENES

[75] Inventor: Stephen E. Belmont, Baton Rouge, La.

[73] Assignee: Albemarle Corporation, Richmond, Va.

[21] Appl. No.: 5,746

[22] Filed: Jan. 19, 1993

[51] Int. Cl.$^5$ .................... C07C 1/20; C07C 1/207
[52] U.S. Cl. .................... 585/358; 585/357
[58] Field of Search ............ 585/357, 358, 359; 568/876, 878, 879

[56] References Cited

U.S. PATENT DOCUMENTS 4,967,033 10/1990 Mahaim .......................... 585/358

FOREIGN PATENT DOCUMENTS 701626 1/1965 Canada .

OTHER PUBLICATIONS

Campbell et al: The Stereochemistry of Pentadienyl-Cyclopentadienyl Cation Rearrangement; Jour. Amer. Chem. Soc., vol. 91, pp. 6404–6410, 1969.
Gannan et al: 1,2,3,4-Tetralmethyl-5-(trifluoromethyl)-cyclopentadienide: A Unique Ligand With the Stereo-Properties of Pentamethyl Cyclopentadienide and the Electronic Properties of Cyclopentadienide, J. Amer. Chem. Soc., vol. 114, pp. 6942–6946, 1992.
Threlkel et al: 1,2,3,4,5-Pentamethylcyclopentadiene, Organic Synthesis, vol. 65, pp. 42–45, 1987.
Okamoto et al: Synthesis of Optically Active γ-Trimethylsilyl-β,γ-epoxy Tertiary Alcohols by the Diastereoselective Addition Reaction of β-Trimethylsilyl-α-β-Epoxy Ketones with Grignard Reagents, Tetrahedron Letters, vol. 41, 1991, pp. S789-S792.
Weber et al: Enantiomerically Pure Tertiary Alcohols by TADDOL-Assisted Addition to Ketones-or How to Make a Grignard Reagent Enantioselective; Angew. Chim. vol. 31, 1992, pp. 84–86 (Int. Edition).
Journal of Organometallic Chemistry, 243 (1983) 119-121, "An Improved Synthesis of 1,2,3,4,5-Pentamethylcyclopentadiene", by Franz X. Kohl, et al.
Organometallics 1988, 7, 1828-1838, "Manipulation of Organoactinide Coordinative Unsaturation . . . " by Carol M. Fendrick, et al.

Primary Examiner—Asok Pal
Assistant Examiner—P. Achutamurthy
Attorney, Agent, or Firm—David M. Bunnell

[57] ABSTRACT

A process is provided for preparing an substituted cyclopentadiene by the steps of (a) reacting a vinyl ketone with a vinyl organometallic compound to form a divinyl tertiary alcohol and (b) dehydrating/cyclizing the tertiary alcohol such as with an acid and/or heat to form the substituted cyclopentadiene.

3 Claims, No Drawings

PREPARATION OF SUBSTITUTED CYCLOPENTADIENES

This process relates generally to the synthesis of substituted cyclopentadienes and more particularly to a two step process for making substituted cyclopentadienes by the reaction of a vinyl ketone with a vinyl organometallic compound such as a vinyl lithium or a vinyl Grignard reagent followed by an acid or thermally catalyzed dehydration/ring closure reaction.

Substituted cyclopentadienes are used as monomers and in forming metallocenes, and especially metallocenes of transition metals such as titanium, zirconium, and hafnium. Such metallocenes are useful components of olefin polymerization catalysts, as is known in the art.

Syntheses of alkyl substituted cyclopentadienes such as pentamethyl and tetramethyl cyclopentadiene which are described, for example, by Kohl et al. in *J. Organomet. Chem.*, 1983, 243 119–121 and Fenderick et al. in *Organometallics*, 1988, 7, b 1828–1838 use a multi-step procedure starting with a long, complex aldol reaction and provide impure products in low yields. The synthesis of pentamethylcyclopentadiene is also described by Threlkel et al., in *Organic Synthesis* 65, 42–45 (1987). The procedure reacts ethylacetate with butenyl lithium to form a tertiary alcohol, followed by ring closure using p-toluene-sulfonic acid. 1,2,3,4-Tetramethyl-5-(trifluoromethyl)cyclopentadiene was prepared by Gassman et al., *J. Am. Chem. Soc.* 1992, 114, 6942–6944 by a similar procedure using ethyl trifluoroacetate in place of ethyl acetate. Burger et al., *Helvetica Chemica Acta*, 57, Fasc. 7 (1974)—Nr 229 pages 2106–2109 discloses at page 1208 (diagram A) the preparation of tetramethylcyclopentenone which starts by reacting 2-butenyl lithium with 2-methyl-2-butenylaldehyde.

This invention provides a fast and inexpensive two step process which can produce substituted cyclopentadienes in high purity and yields.

In accordance with this invention there is provided a process for preparing a substituted cyclopentadiene, said process comprising the steps of (a) reacting a vinyl ketone with a vinyl organometallic compound to form a divinyl tertiary alcohol and (b) dehydrating/cyclizing said alcohol to form said substituted cyclopentadiene.

The process of the invention forms substituted cyclopentadienes by the reaction of a vinyl ketone having the formula $HCR^1=CR^2C(O)R^3$ with a vinyl organic compound, which is preferably either a vinyl alkali metal compound or a vinyl Grignard reagent, to form a divinyl tertiary alcohol which is then treated with acid and/or heated to accomplish dehydration/ring closure as follows:

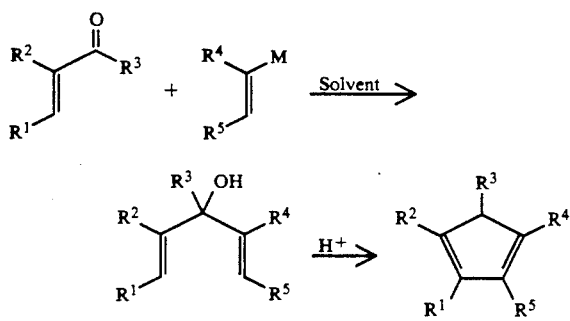

wherein $R^3$ is hydrocarbyl, substituted hydrocarbyl, $R^1$, $R^2$, $R^4$, and $R^5$ are individually hydrogen, hydrocarbyl, substituted hydrocarbyl, or silahydrocarbyl, and M is either alkali metal or MgX, where X is halogen. $R^3$ must be hydrocarbyl or substituted hydrocarbyl in order to achieve ring closure and $R^2$ and $R^4$ are preferably hydrocarbyl, substituted hydrocarbyl or silahydrocarbyl to facilitate cyclization.

By proper selection of the starting vinyl ketones and vinyl organometallic reactants, the process can be used to provide mono- through pentaalkyl substituted cyclopentadienes and especially di-through pentaalkyl substituted cyclopentadienes.

The hydrocarbyl and substituted hydrocarbyl R groups on the reactants include alkyl, substituted alkyl, aryl and substituted aryl. The alkyl can be straight, branched chain or cyclic alkyl. The aryl groups include, for example, phenyl, naphthyl and the like. The alkyl and aryl groups can contain one or more substituents which do not interfere with or participate in the process. Non-limiting examples of such substituents include aromatics, (i.e. phenyl, benzyl), ethers, amides, protected alcohols, protected ketones and the like. The number of carbon atoms in the R groups is not critical but, when the product is to be used in forming metallocenes for use as olefin polymerization catalysts, R groups containing from 1 to about 30 carbon atoms, and especially alkyl groups or substituted alkyl groups which contain from 1 to about 20 carbon atoms, are preferred.

Non-limiting examples of vinyl ketones include methyl isopropenyl ketone, 3-buten-2-one, 2-octen-4-one, 2-hepten-4-one, 4-phenyl-3-buten-2-one, trans-chalcone, $(C_6H_5C=CHC(O)C_6H_5)$ 3-octen-2-one, 4-methyl-3-buten-2-one, and the like.

The vinyl organometallic reactants are preferably vinyl alkali metal compounds such as vinyl sodium and especially vinyl lithium compounds or vinyl Grignard reagents such as vinyl magnesium bromides and chlorides having the formula $HCR^5=CR^4M$ where $R^4$, $R^5$ and M are as defined above. The compounds are either commercially available or can be prepared as known in the art from the corresponding vinyl halides, and especially vinyl bromides, by reaction with the alkali metals.

The reaction of the vinyl ketone with the vinyl organometallic compound is preferably carried out in from about 0.5 to 10 parts by weight per part by weight of reactants of organic solvent having a boiling point below about 45° C. Non-limiting samples of suitable solvents include diethyl ether, diethyl ether/pentane, t-butyl methyl ether and the like. The vinyl ketone and vinyl organometallic compounds are preferably used in proportions of from about 0.5 to 1.5 mole of vinyl ketone per mole of vinyl organometallic compound.

The reaction can be carried out at ambient temperatures, but higher or lower temperatures can be used. Temperatures of from about 0° to 40° C. are preferred. Reaction times are generally from about ½ to 1 hours. After the reaction is completed, the reaction mixture can be quenched with water. The product divinyl tertiary alcohol is contained in the organic solvent layer from which it can be recovered.

The tertiary alcohol intermediate prepared above is then reacted with an acid and/or heated to accomplish dehydration/ring closure and form the substituted cyclopentadiene product.

Non-limiting examples of suitable acids for use in the ring closure reaction are mineral acids, such as sulfuric and phosphoric acid and organic acids, such as toluene sulfonic acid and trifluoromethane sulfonic acid. Especially preferred are strongly acidic cation exchange resins such as Amberlyst-15, a sulfonated polystyrene, resin or Dowex-50 resin and the like.

A suitable reaction procedure is to stir or otherwise mix the resin and the alcohol, which is dissolved in 1 to 10 parts by weight per part by weight of reactants of organic solvent such as, for example, pentane, isopentane, hexane, heptane, ether and the like, for from about 1 to 6 hours to accomplish ring closure. Ambient temperature can be used but higher or lower temperatures can also be used. Reaction temperatures of from about 10° to 30° C. are preferred for acid dehydration/cyclization. For thermal dehydration/cyclization higher temperatures of up to about 200° C. would be used. Proportions of acid and alcohol of from about 0.05 to 0.3 parts by weight of acid per part by weight of alcohol are preferred.

After the ring closure reaction is completed, the reaction mixture is treated to remove the acid, such as with sodium dicarbonate for soluble acids or filtration for acidic resins. The product can then be recovered from the organic solvent by conventional techniques. The product can be purified either by chromatography, using for example, silica or alumina or by distillation.

The process is further illustrated by, but is not intended to be limited to, the following examples.

EXAMPLE 1A

Lithium metal (2.56 grams, 366 mmol) was put into an argon purged 3-neck flash and 13 mL of diethyl ether and 1 mL of butenyl bromide were added with stirring. An additional 115 mL of diethyl ether were added and then the remaining 16.1 mL of bromide (total bromide 22.7 grams, 168 mmol) over 30 minutes. The reaction mixture was stirred for an additional 30 minutes after which 10.1 grams (120 mmol) of methyl isopropenyl ketone in 5 mL of diethyl ether were added over 15 minutes. The reaction mixture was stirred for 30 minutes, quenched with 100 mL water, and the ether layer containing the product 2,3,4-trimethyl-1,4-hexadien-3-ol was dried, filtered and condensed. The yield of product having a purity of 93% was 15.74 grams (94%).

EXAMPLE 1B

The tertiary alcohol product (15.7 grams) prepared in Example 1A was dissolved in 100 mL of pentane, 1.3 grams of Amberlyst-15 resin were added and the mixture was stirred. The reaction was monitored by gas chromatography and was 98% complete after 2 hours. The reaction mixture was washed down a 6"×141 plug of basic alumina and condensed. The yield of crude product was 11.54 grams (85%) of which 74% was 1,2,3,4-tetramethylcyclopentadiene. The true yield of pure 1,2,3,4-tetramethylcyclopentadiene was 8.5 grams or 62%.

EXAMPLE 2A

Lithium metal (60 grams, 8.5 mol) was put into an argon purged 5 L, 3-neck flask and 250 mL of diethyl ether and 10 grams of butenyl bromide were added with stirring. After initiation an additional 2.25 L of diethyl ether were added and then the remaining 490 grams of bromide (total bromide 500 grams, 3.7 mol) were added over a period of 50 minutes with cooling. The reaction mixture was then stirred for 45 minutes at ambient after which 311 grams (3.7 mol) of methylisopropenyl ketone were added over 45 minutes with cooling. The reaction mixture was then stirred for 60 minutes at room temperature and thereafter 1.5 L of $H_2O$ were slowly added. The ether layer containing the 2,3,4-trimethyl-1,4-hexadien-3-ol was separated, dried, and filtered. The product was used as is in Example 2B.

EXAMPLE 2B

The tertiary alcohol product prepared above (and still in the original ether solvent) was cooled to 0° C. and 50 grams of Amberlyst-15 resin were added. The mixture was stirred for 6.5 hours at room temperature, (two additional 10 gram portions of Amberlyst-15 resin were added after 1 and 3 hours), filtered and condensed. The yield of crude product was 456.1 grams (66.2% alkyl cyclopentadiene product, 14.1% solvent, 19.7% impurities) 61% and the yield of pure 1,2,3,4-tetramethylcyclopentadiene was 67% (two-step yield).

Comparison 1

When the process according to Example 1 was repeated except using ethyl formate in place of the ketone which produced a secondary alcohol intermediate, total decomposition occurred when the secondary alcohol was reacted with the acid resin. No tetramethyl cyclopentadiene product was detected.

Example 3A

4-Methyl-3-buten-2-one (98% pure 2.0 grams, 24.4 mmol) was purged with Ar in a 100 ml round bottom flash and 20 mL of diethyl ether was added. The contents of the flask were cooled to 0° C. and 34 ml (34 mmol) of the Grignard reagent, vinyl magnesium bromide, were slowly added over 10 minutes. The reaction mixture was stirred for an additional 75 minutes, quenched with 40 mL of saturated aqueous $NH_4Cl$ and then 125 mL of water were added. Aqueous and organic layers separated and the aqueous layer was extracted with 40 mL of diethyl ether. The organic layer and ether extract containing the product 3-methyl-1,4-hexadiene-3-ol were dried, filtered and concentrated.

EXAMPLE 3B

The tertiary alcohol product prepared in Example 3A was dissolved in 30 mL of pentane and 500 mg of Amberlyst-15 resin were added. The reaction stopped after 18 hours. The 1,3-dimethylcyclopentadiene product appeared to have formed its Dieis-Alder dimer. The dimer can be readily converted back to the monomeric form for example by distillation using a Vigreax column and collection of the distillate monomer at low temperature, as is well known in the art.

Similarly, 1-butene-3-methylcyclopentadiene can be synthesized from 2-octen-4-one and vinyl lithium or vinyl magnesium bromide. The Grignard reagent, $CH_2=CHMgBr$, is commercially available.

What is claimed is:

1. A process for preparing a substituted cyclopentadiene said process comprising the steps of (a) reacting a vinyl ketone with a vinyl organometallic compound to form a divinyl tertiary alcohol and (b) dehydrating/cyclizing said alcohol to form said substituted cyclopentadiene in the presence of an acidic cation exchange resin, wherein (a) said vinyl ketone has the formula $HCR^1=CR^2C(O)R^3$, wherein $R^1$ is hydrogen or $C_1$ to $C_{30}$ alkyl and $R^2$ and $R^3$ are independently $C_1$ to $C_{30}$ alkyl, (b) said vinyl organometallic compound has the formula $HCR^5=CR^4M$, wherein $R^4$ is $C_1$ to $C_{30}$ alkyl, $R^5$ is hydrogen or $C_1$ to $C_{30}$ alkyl and M is Li, Na or MgX, where X is halogen, and (c) at least one of $R^1$ and $R^5$ is hydrogen.

2. The process according to claim 1 wherein said metal is lithium.

3. The process of claim 1 wherein said vinyl ketone is methyl isopropenyl ketone said vinyl organometallic compound is 2-lithio-2-butene and said substituted cyclopentadiene is 1,2,3,4-tetramethylcyclopentadiene.

* * * * *